(12) United States Patent
Leibig et al.

(10) Patent No.: US 7,658,714 B2
(45) Date of Patent: Feb. 9, 2010

(54) INTELLIGENT ULTRASOUND EXAMINATION STORAGE SYSTEM

(75) Inventors: Ruth E. Leibig, Palo Alto, CA (US); Ken M. Fowkes, Mountain View, CA (US); Ismayil M. Guracar, Redwood City, CA (US); Christopher S. Hedgecock, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/698,670

(22) Filed: Oct. 31, 2003

(65) Prior Publication Data

US 2005/0096539 A1    May 5, 2005

(51) Int. Cl.
    *A61B 8/00*    (2006.01)
(52) U.S. Cl. .................. 600/443; 600/437; 382/128
(58) Field of Classification Search ................ 600/437, 600/443; 382/128
    See application file for complete search history.

(56) References Cited

U.S. PATENT DOCUMENTS

| | | | | |
|---|---|---|---|---|
| 5,315,512 A * | 5/1994 | Roth | .......................... | 600/442 |
| 5,566,674 A | 10/1996 | Weng | .................... | 128/660.07 |
| 5,575,286 A | 11/1996 | Weng et al. | ............. | 128/653.1 |
| 5,709,210 A | 1/1998 | Green et al. | .......... | 128/661.07 |
| 5,782,766 A | 7/1998 | Weng et al. | ................. | 600/443 |
| 5,810,007 A | 9/1998 | Holupka et al. | | |
| 5,846,202 A * | 12/1998 | Ramamurthy et al. | ....... | 600/450 |
| 5,873,830 A * | 2/1999 | Hossack et al. | ............. | 600/447 |
| 5,920,317 A * | 7/1999 | McDonald | ................... | 715/853 |
| 5,924,991 A * | 7/1999 | Hossack et al. | ............. | 600/443 |
| 5,959,622 A | 9/1999 | Greer et al. | | |
| 5,976,088 A * | 11/1999 | Urbano et al. | ............. | 600/443 |
| 6,012,458 A * | 1/2000 | Mo et al. | ..................... | 600/437 |
| 6,014,473 A | 1/2000 | Hossack et al. | ............. | 382/294 |
| 6,042,545 A * | 3/2000 | Hossack et al. | ............. | 600/443 |
| 6,056,691 A | 5/2000 | Urbano et al. | ............. | 600/443 |
| 6,102,865 A | 8/2000 | Hossack et al. | ............. | 600/459 |
| 6,132,376 A | 10/2000 | Hossack et al. | ............. | 600/443 |
| 6,201,900 B1 | 3/2001 | Hossack et al. | ............. | 382/294 |
| 6,222,948 B1 | 4/2001 | Hossack et al. | ............. | 382/294 |
| 6,228,030 B1 * | 5/2001 | Urbano et al. | ............. | 600/443 |
| 6,231,508 B1 | 5/2001 | Miller et al. | | |
| 6,231,510 B1 | 5/2001 | Negrin et al. | | |
| 6,315,730 B1 * | 11/2001 | Hoff et al. | .................... | 600/458 |
| 6,352,508 B1 | 3/2002 | Pang et al. | ................... | 600/443 |
| 6,360,027 B1 | 3/2002 | Hossack et al. | ............. | 382/294 |
| 6,364,835 B1 | 4/2002 | Hossack et al. | ............. | 600/443 |
| 6,447,450 B1 * | 9/2002 | Olstad | ........................ | 600/437 |
| 6,511,426 B1 * | 1/2003 | Hossack et al. | ............. | 600/437 |
| 6,542,626 B1 * | 4/2003 | Brouwer et al. | ............. | 382/128 |
| 6,554,770 B1 | 4/2003 | Sumanaweera et al. | ..... | 600/443 |
| 6,574,304 B1 * | 6/2003 | Hsieh et al. | ................... | 378/62 |
| 6,673,017 B1 * | 1/2004 | Jackson | ...................... | 600/437 |
| 6,716,172 B1 | 4/2004 | Kerby et al. | | |

* cited by examiner

*Primary Examiner*—Brian Casler
*Assistant Examiner*—John F Ramirez

(57) ABSTRACT

An intelligent ultrasound examination storage system is disclosed, which permits a sonographer to focus entirely on the examination process while the system analyses image data and marks events of interest for post-examination review or storage.

41 Claims, 3 Drawing Sheets

INTELLIGENT ULTRASOUND EXAMINATION STORAGE SYSTEM

BACKGROUND OF THE INVENTION

This invention is in the field of diagnostic medical ultrasound imaging.

Diagnostic medical ultrasound imaging systems have the ability to store images in random access memory, to a hard disk, to a server over a network, to videotape, or to other storage devices. However, storing an entire ultrasound exam can be unwieldy, both in terms of the storage space required (irrespective of the storage media), and in terms of later review. Accordingly, some ultrasound systems permit the user to select interesting portions of the examination. These portions can be marked for later review within the entire examination archive, or can be stored as a discrete excerpt of the examination.

The process of ultrasound examination is challenging. Sonographers require substantial training in anatomy, ultrasound theory and instrumentation, and image analysis interpretation, in order to be able to reliably obtain a useful examination. Moreover, the ultrasound examination process itself generally consumes the full attention of the sonographer.

SUMMARY OF THE INVENTION

While this Summary of the Invention is intended to provide a context for appreciating the discussion of the Detailed Description of preferred embodiments below, it is not intended to limit the scope of the invention. Rather, the invention is limited only by the scope of the appended claims, including both their literal wording and all equivalents thereto.

Accordingly, a first aspect of the instant invention is directed to an improvement in a diagnostic medical ultrasound system. The improvement comprises an automatic event recognition processor, which can recognize at least one distinguished event constituting a subset of an ultrasound examination, and select the event for further review. The improved ultrasound system automatically marks and/or stores portions of an ultrasound examination associated with the events of interest, and/or halts the marking and/or storing of a portion of the ultrasound examination.

According to another aspect of the invention, the improvement to a diagnostic medical ultrasound system comprises an intelligent examination storage system, which automatically recognizes and marks or stores one or more non-repeating subsets of an ultrasound examination. One or more pairs of distinguished events bracket these non-repeating subsets.

According to yet another aspect of the invention, a method is provided for storing data by a diagnostic medical ultrasound system. The method comprises the steps of: (1) inputting ultrasound exam data to an event recognition processor, and (2) processing the exam data by (a) reviewing a sequence of data input sets, (b) determining, as a result of the review, whether a distinguished event has occurred, and, (c) if a distinguished event has occurred, selecting a subset of the data input sets for marking or storage, or for cessation of marking or storage. Finally, the selected image data are marked or stored, or marking and/or storing are stopped, without the need for user intervention.

The invention, along with its attendant objects and advantages, will be best understood in connection with the following Detailed Description of the Preferred Embodiments, reviewed in conjunction with the drawings.

DETAILED DESCRIPTION OF THE PREFERRED EMBODIMENTS

Figure 1:
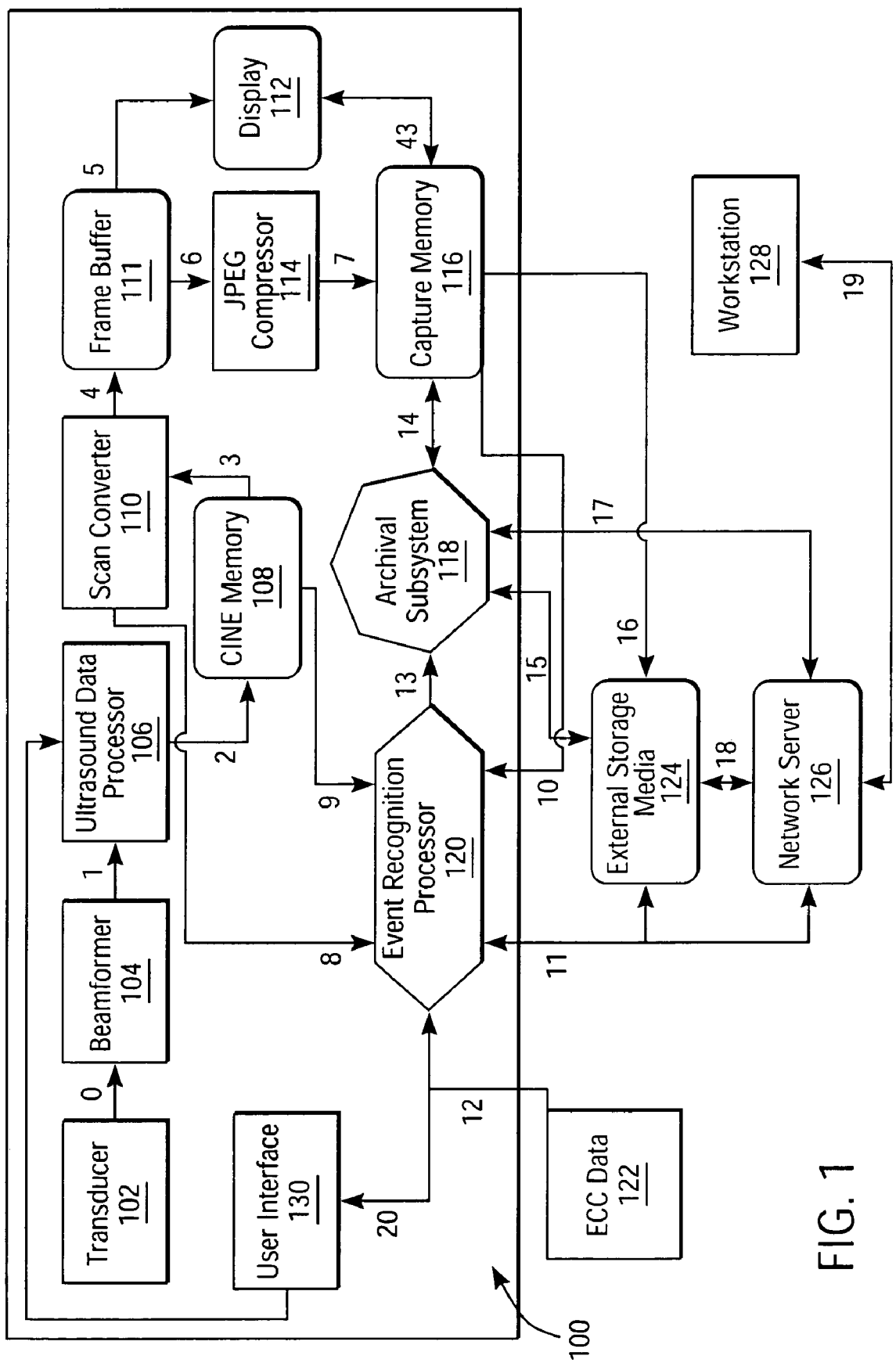
FIG. 1 shows a block diagram of an intelligent ultrasound examination storage system including an event recognition processor.

The following Detailed Description of Preferred Embodiments is intended to be illustrative and not limiting, as the scope of the invention is intended to be commensurate with the full breadth of the appended claims, including all equivalents thereto. Moreover, the features and preferred embodiments described herein can be used separately, or in combination, in various embodiments of the invention.

As a result of the skill level and attention required to competently perform an ultrasound examination, a need exists for an improved ultrasound system that can automatically and intelligently select portions of an exam for marking for further review or for storage. U.S. patent application Ser. No. 10/328,426 to Kerby et al., assigned to the assignee of the present invention, filed Dec. 23, 2002, and entitled, "Medical Diagnostic Ultrasound Imaging System and Method for Displaying a Portion of an Ultrasound Image," and hereby fully incorporated by reference into this specification, describes a feature in an ultrasound system that can, while storing an image clip pursuant to user input, automatically capture a larger part of the image than selected by the user for storage, and can also capture portions of the exam immediately preceding and immediately following the user selected portions. Nevertheless, it is up to the sonographer to indicate the portions of the examination that the user deems of interest.

The improvements described herein are directed to relieving the sonographer of the need to determine, during the ultrasound examination, which sections of the examination are worthy of being marked for further review or stored. Instead, while the sonographer focuses entirely on obtaining the best possible image, the ultrasound system analyzes the images obtained by the sonographer and automatically recognizes when a "distinguished event" has occurred that warrants storing or marking a selected part of the examination. For the purposes of this specification, a "distinguished event" is any non-cyclical event of interest, or, a subset of cycles of a series of cyclical events in an ultrasound exam. Such an event is recognized by an event recognition processor, which takes as input ultrasound data (at any stage, e.g., from the ultrasound beamformer, data processor, scan converter, capture memory, or hard disk), analyses the data, and determines whether or not a particular transition has occurred. Upon recognition of such a "distinguished event," the event recognition processor can mark and/or store (or cause to be marked and/or stored) data at, before, and/or after the distinguished event. In some embodiments, the event recognition processor can also recognize "distinguished events" that call for cessation of the marking or storing process for future image data, and upon recognition of such events, the event recognition processor can terminate the marking and/or storage, or cause it to be terminated, for example, until the next distinguished event. Typically in such embodiments, a first distinguished event is associated with the beginning of a series of image data sets to be stored and a second distinguished event is associated with the end of such a series (or image clip).

While in many embodiments described below, the event recognition processor operates on image data produced during the course of a real-time ultrasound examination, the invention is not so limited. Rather, in other embodiments, the event recognition processor can take as input image data sets from part of, or from a whole, previously stored ultrasound exam. This data can come either from an external workstation or network server, or from storage integral to the ultrasound system. The event recognition processor can review these image data sets, recognize distinguished events therein, and store (or cause to be stored) a smaller file that includes image data sets associated with these events while discarding (or causing to be discarded) image data sets that are not likely to be of interest.

In FIG. 1, an ultrasound system 100 is shown having, and communicating with, various types of storage capabilities and accessories, as well as a network server 126. The drawing is simplified so as not to obscure the various features of the preferred embodiments with ultrasound system details that are known in the art. In the illustrated embodiment, an ultrasound system 100 is in communication with a workstation 128 via external storage media 124 (such as but not limited to, a hard drive, a CD-ROM, or a memory stick) and/or the network server 126. In this environment, ultrasound images and other information can be saved in digital form for later review in the ultrasound system 100 or on the workstation 128. The workstation 128 can be a computer comprising a display device, a user interface, and a processor that runs image review software that allows a user to retrieve and review a stored digital image and perform measurements and other post-processing activities on the image. Preferably, the external storage media 124 operates under a Digital Imaging and Communications in Medicine (DICOM) exchange media format, and the network server 126 is DICOM compliant. Although DICOM format is preferred because it is a standard for medical workstations, other formats and viewers (such as Audio Video Interleave (AVI), which is a special case of the Resource Interchange File Format (RIFF)) can be used.

The basic ultrasound system 100 blocks shown in this embodiment are user interface 130, transducer 102, beamformer 104, ultrasound data processor 106, CINE memory 108, scan converter 110, frame buffer 111, display 112, JPEG compressor 114, capture memory 116, archival subsystem 118, and event recognition processor 120. External storage media 124, network server 126, ECG data output 122, and workstation 128 are generally accessories to the ultrasound system 100, but could optionally be wholly or partly integrated therewith. Alternatively, the ultrasound system 100 could include the bare minimum functionality of the transducer 102, beamformer 104, data processor 106, scan converter 110, and display 112, with some or all of the balance of the blocks in FIG. 1 being provided as separate accessories thereto. Accordingly, the broadest conception of the invention herein does not depend on where the line is drawn between the ultrasound system components on the one hand, and the number or location of storage capabilities and accessories on the other hand, so long as, taken together, the system provides for automatic event recognition and either marking or storage of the recognized events, or discarding of portions of an ultrasound exam that are of insufficient interest to warrant further review.

The various ultrasound system 100 blocks that process data, such as but not limited to the beamformer 104, ultrasound data processor 106, scan converter 110, display 112, JPEG compressor 114, archival subsystem 118, and event recognition processor 120, can be implemented in core logic, as part of one or more application specific integrated circuits (ASICs) and/or field programmable gate arrays (FPGAs). Alternatively, or in addition, they can be implemented in software on a digital signal processor or a general-purpose microprocessor, in a manner that will be apparent to one of ordinary skill in the art in light of the discussion and drawings herein. As a matter of design choice, they can be implemented together or separately, and they can be implemented in the same way or in different ways.

During an ultrasound examination, a sonographer selects an imaging mode through the user interface 130, and makes contact between the transducer 102 and a patient. The beamformer 104 controls hardware that applies a voltage to the transducer 102 causing it to vibrate and transmit sound waves into, and receive echoes from, the body of the patient (generally a human, but animals also receive ultrasound examinations). The echo signals from the patient's body are passed from the transducer via path 0 to a beamformer 104. The output 1 of beamformer 104 is passed to ultrasound data processor 106. The ultrasound data processor 106—which can take the form of one or more general processors, digital signal processors, application specific integrated circuits, logic devices, analog devices, or other electrical components—performs, filtering, signal processing and other functions used to generate an ultrasound image. (It should be noted that the circuitry included in the beamformer 104 and the ultrasound processor 106 is a matter of design choice, and that optionally, the functionality of each can be combined.) The exact function of the ultrasound data processor 106 can vary depending on what imaging mode is invoked via user interface 130 (e.g., B-Mode using fundamental or harmonic imaging, M-Mode, color flow, spectral Doppler, stress echo, and contrast agent imaging, or combinations of these).

Moreover, the user interface 130 can invoke certain "presets" which optimize imaging in an application-specific manner, based on based on anatomy, exam type, and/or exam protocols. Examples of such application-specific pre-sets include obstetrics, stress echocardiography, ECG imaging, cardiac imaging using a combination B-mode and Color Doppler modalities, contrast agent imaging, and abdominal, thyroid, vascular, testicular and breast imaging.

The user interface 130 can be configured to receive audio or visual feedback, signaling beginning and/or end of automatic image data capture of "distinguished events" and associated image data, in accordance with a preferred embodiment of the invention, as will be more fully described below.

The ultrasound data processor 106 outputs ultrasound data to the scan converter 110, either directly, or as shown in the embodiment of FIG. 1, through paths 2 and 3, via CINE memory 108 (random access memory). CINE memory 108 captures a rolling stream of the most recent ultrasound data, which can be played back on the spot and marked for later review or storage.

The data being input to the scan converter 110 via path 3 can be in a proprietary, hardware-dependent format. The scan converter 110 transforms the data into a standard pixel format (e.g., JPEG, RGB, YCbCr) so that an ultrasound image can be displayed on the display device 112. For example, the scan converter 110 can convert the ultrasound data from a polar coordinate format to a Cartesian coordinate format. While ultrasound images coming from the scan converter are often referred to as "image frames," or "frames of image data," this invention also applies to modalities that have a strip-based display, such as spectral Doppler, ECG or respiratory traces, or M-mode. Accordingly, the ultrasound data will generally be referred to as "image data sets," which is intended to include, in addition to frames of image data, ECG and respiratory traces, and image data before scan conversion (such as would be the case where image data from the CINE Memory block 108 were input into the event recognition processor 120 via path 9 in FIG. 1).

A post-scan converted ultrasound image can be output from the scan converter 110 to a frame buffer 111 via path 4, and then from there to the display 112 via path 5, or to the JPEG (i.e., the image compression standard defined by the Joint Photographic Experts Group) compressor 114 via path 6. (Of course, other compression algorithms could be used instead of JPEG, or the compression step can be omitted entirely.) The compressed JPEG images can then be transferred via path 7 to capture memory 116. As used herein, the term "ultrasound image" refers to either a single image frame or a plurality of image frames or image data sets, and may also be referred to herein as a "multi-frame ultrasound image" or an "image clip." From capture memory 116, the ultrasound images can be transferred to archival subsystem 118 via path 14. Archival subsystem 118 can modify multi-frame ultrasound images to be DICOM compliant and store them or cause them to be stored in the DICOM format.

Event recognition processor 120 can obtain ultrasound images from any or all of a variety system blocks, such as from the scan converter 110 via path 8, the CINE memory 108 via path 9, the capture memory 116 via path 10, the external storage media or network server via path 11, or the ECG data output 122 via path 12. The function of the event recognition processor 120 is to review a series of image data sets and determine whether a transition has occurred in the series that would constitute a "distinguished event." The event recognition processor 120 preferably selects one or more algorithm blocks to execute this review, based on the imaging modality and/or the preset selected by the sonographer through user interface 130. The event recognition processor 120 can optionally also be configured to provide audio and/or visual feedback via path 20 to the user interface 130 indicating recognition of a distinguished event (or to cause such feedback to be applied by sending a signal to another system block, such as archival subsystem 118 via path 13). Different types of audio and/or visual signals can be provided to alert the sonographer to the system's recognition of distinguished events that begin an image data set or image clip or interest, and of such events that terminate the data set or image clip. Examples of such signals are: tones of a different pitch; an LED that displays a counter, which increments to the next number upon the termination of storage or an image clip or portion of the exam; and/or an icon that emulates a recording tape, displayed on a portion of display 112 or elsewhere on user interface 130.

As shown in the embodiment of FIG. 1, external storage media 124 can receive data from capture memory 116 via path 16, network server 126 via path 18, and workstation 128 via path 19 and the network server 126. Moreover, the event recognition processor 120 can receive data from workstation 128 via path 19 and network server 126. The network server 126 can optionally exchange information with the event recognition processor 120 and/or the archival subsystem 118 via paths 11 and 17 respectively. Similarly, the external storage media 124 can be configured to have a bi-directional interface with event recognition processor 120 via path 11 and/or with archival subsystem 118 via path 15. Accordingly, in some embodiments, the intelligent ultrasound examination storage system can sort through stored ultrasound exams, even from other ultrasound systems, recognize distinguished events from those exams, and store subsets of the previously stored exams based on the recognition of those events. These smaller, sorted stored files facilitate review and can save storage space by replacing the original files. The exams can be reviewed, for example, either on display 112 or workstation 128.

Figure 2:
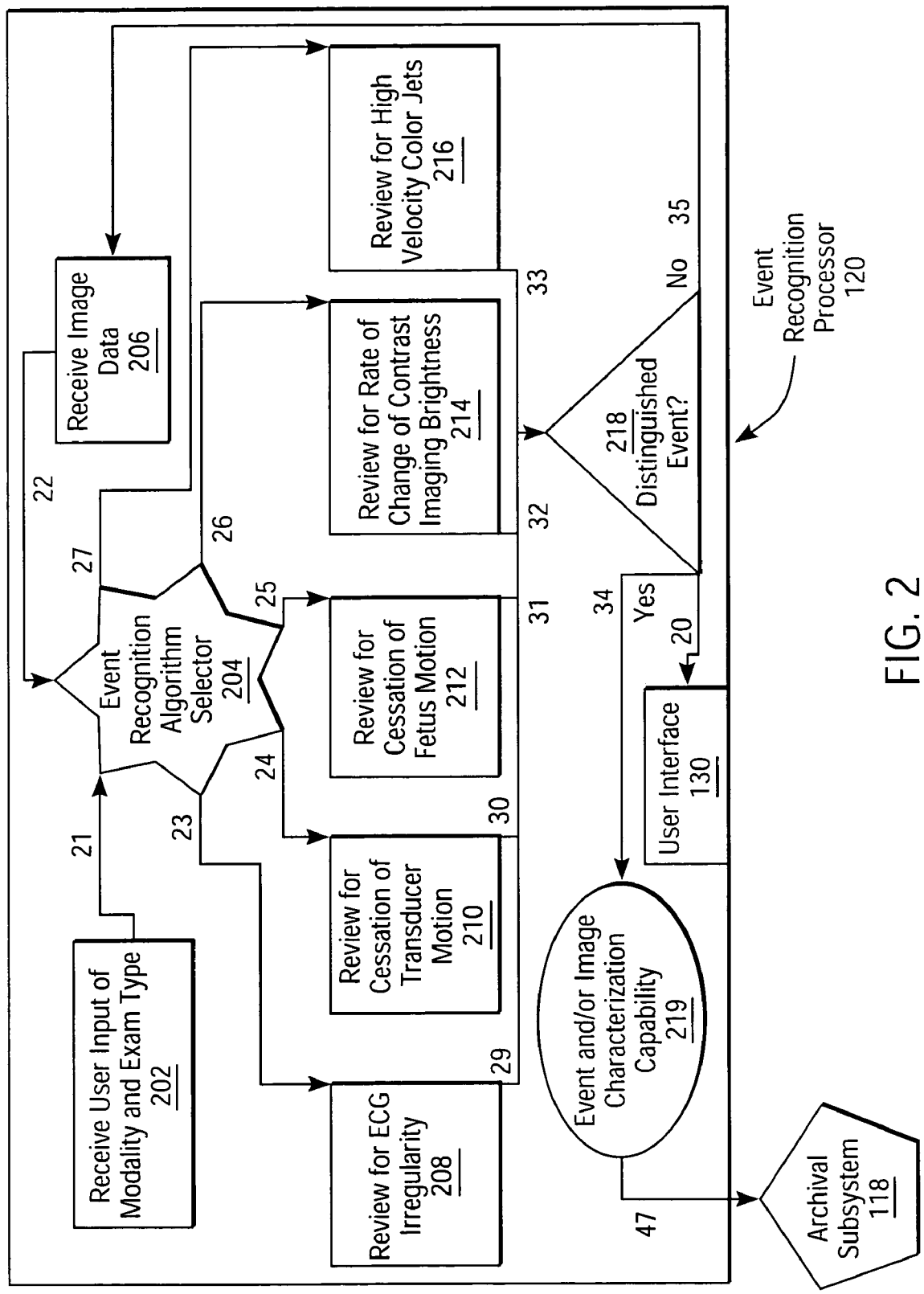
FIG. 2 shows an example of the process flow of the event recognition processor of FIG. 1, having a plurality of event recognition algorithm blocks, various ones of which can be invoked based on the user's selection of a diagnostic ultrasound imaging modality, or an application-specific pre-set.

As shown in the flowchart of FIG. 2, in one embodiment of the invention, the event recognition processor 120 has an event recognition algorithm selector 204, which receives as input: (1) the user input of modality and examination type as represented by block 202 via path 21, and (2) image data sets as represented by block 206 via path 22. The event recognition algorithm selector 204 applies different review algorithms, such as but not limited to those shown in blocks 208, 210, 212, 214 or 216 (via respective paths 23, 24, 25, 26, and 27), to the image data sets from 206 depending upon the initial user input (via user interface 130 in FIG. 1) received by event recognition processor 120 in block 202. It will be appreciated that this initial user input occurs prior to the ultrasound examination, as part of the sonographer's process of setting up the exam, and therefore does not detract from the "automatic" nature of the intelligent ultrasound examination storage system described herein. The nature of this user input is in distinction to the situation where the sonographer, during the examination, causes an ultrasound image or image clip to be stored and marked for later review, thereby diverting his or her attention from the examination process while it is ongoing. It will also be appreciated that allowing the sonographer to choose to manually store segments of the examination, in addition to those segments that are stored automatically by virtue of the intelligent ultrasound examination storage system described herein, would provide greater flexibility to the sonographer without detracting from the invention.

The review algorithms shown in blocks 208, 210, 212, 214 or 216 are designed to detect transitions between states, or "distinguished events," in different types of ultrasound examinations. Thus, for example, in an ECG (electrocardiograph) exam, the algorithm in block 208 of the event recognition processor 120 will look for a substantial difference in the duration of a heartbeat, as measured by the distance between R-wave peaks in a cardiac trace. More specifically, the algorithm in block 208 could, for example, look for R-wave peaks that are substantially closer together than the norm for a particular patient as determined by the average R to R distance for other beats during the examination, or substantially closer together than a pre-selected standard. Such an algorithm would recognize such peaks that were, for example, 50% closer than average for the previous 10 beats, and recognize them as "distinguished events" in block 218 of FIG. 2. The "normal," regularly recurring and evenly spaced, R-wave peaks would not qualify as "distinguished events," because they are part of a regularly repeating cycle. One of skill in the arts of ultrasound instrumentation and echocardiography will recognize that other aspects of the cardiac trace could alternatively or in addition be monitored for irregularities by algorithm block 208 of the event recognition processor 120 of FIG. 2, and review of any such irregularities is of course within the scope of this invention.

Figure 3:
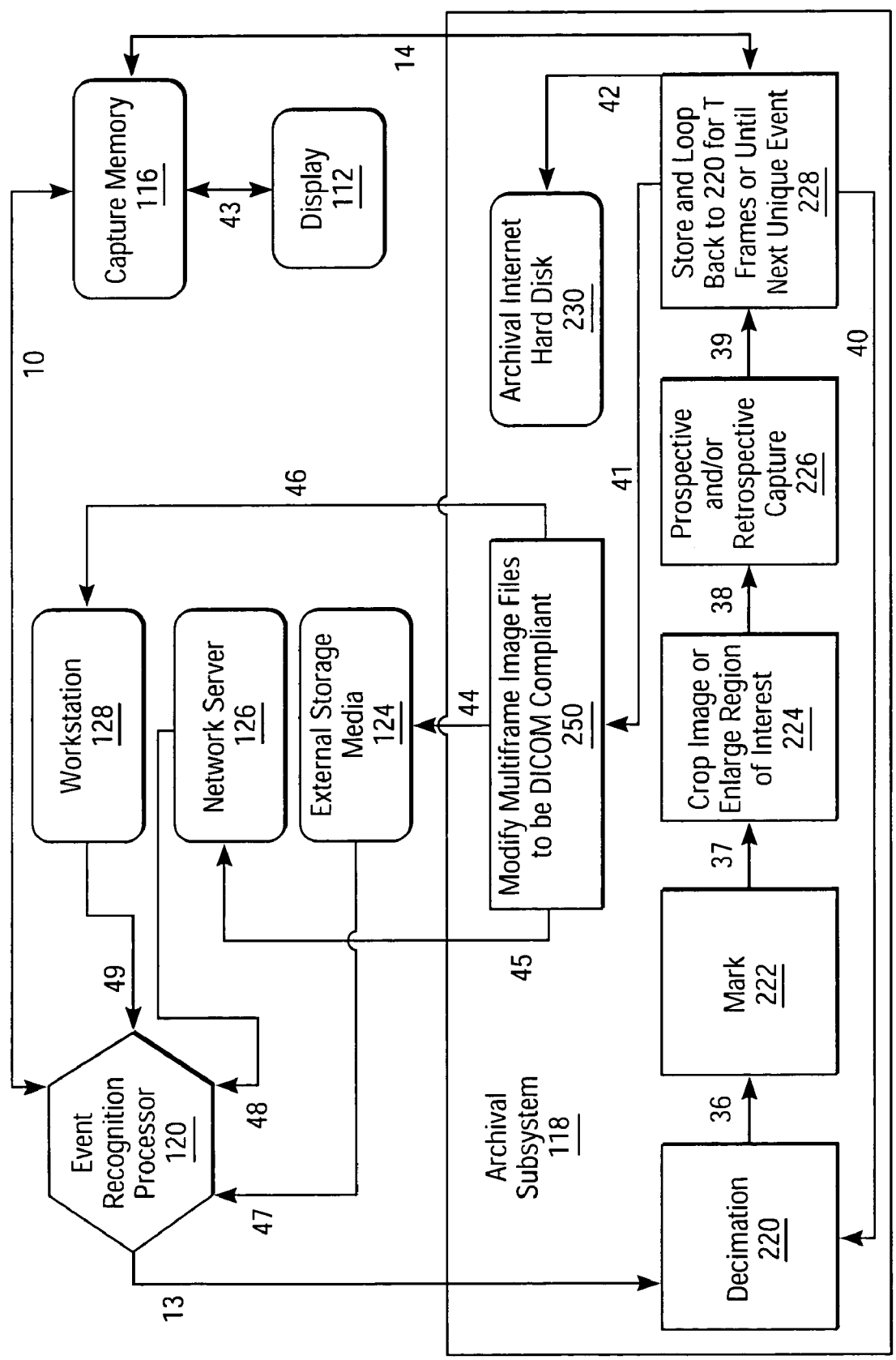
FIG. 3 shows an example of the process flow of the archival subsystem of FIG. 1, having a plurality of post processing blocks and the ability to mark and/or store an image or series of images or image data sets.

Once the image is so recognized as a distinguished event, image data are passed via path 13 of FIG. 1 from the event recognition processor 120 to the archival subsystem 118, where any or all of post processing steps shown in FIG. 3 in blocks 220 (decimation), 222 (marking), 224 (cropping or enlarging), 226 (prospective or retrospective capture) or 228 (storage) can be invoked. Alternatively, upon recognition of a distinguished event, event recognition processor could send a control signal (rather than image data) along path 13 to archival subsystem 118, which would in turn process the image data from the capture memory 116. In yet another alternative, image data sets and application-specific input and/or ultrasound modality information could be input to the event recognition processor 120 from workstation 128 via path 19, network server 126 and path 11, or from external storage media 124 via path 11. Image data associated with distinguished events could be passed via path 13 to archival subsystem 118 for post-processing and review on display 112. Examples of post-processing steps are schematically shown in FIG. 3 and will be discussed in greater detail below.

Returning to FIG. 2, in a B-mode obstetrics exam, the event recognition processor 120 will apply an algorithm in block 212 that targets periods of low mobility of the fetus, because such periods provide for optimum imaging. In particular, a key part of the obstetrics examination is to take measurements of various portions of the fetus, and this is easier to do when the fetus is still than when it is in motion. Accordingly, the algorithm in block 212 will review the image data for cessation of fetus motion, and the algorithm in block 218 will recognize as distinguished event frames or series of frames where motion between successive frames is below a certain threshold, e.g., less than an average of 1 cm/sec.

Once again, when a distinguished event is recognized, the image data are passed to one or more of the post processing blocks 220 to 228 of archival subsystem 118 shown in FIG. 3. For example, the archival subsystem can be designed so that in this particular modality a relatively substantial amount of decimation (a low retention fraction, as described in more detail below) is applied in block 220. This would tend to give the stored or marked image a "jerky" quality, but would facilitate the sonographer's or physician's review of the image data to take fetal measurements. The (optionally decimated) frames of interest could be marked for later review on the ultrasound system in block 222. The image could be cropped, if desired, in block 222, to automatically exclude information that is clearly irrelevant. In block 226, prospective or retrospective capture could be invoked. Thus, for example, the archival subsystem 118 could automatically capture a first preselected number of image data sets before the distinguished event and a second preselected number of image data sets after the distinguished event. In one particularly preferred embodiment, the intervals of low fetus motion are tracked as distinguished events during the entire exam, and the longest of these intervals are preserved by marking and/or storage. More specifically, the transition from a moving fetus to a relatively still fetus would constitute a first distinguished event of a pair of distinguished events, and the transition back from a relatively still fetus to a moving fetus would constitute a second distinguished event of such a pair. Image data sets between said pairs of distinguished events would be captured, with preference being given to those pairs of events that together bracket image clips of the longest duration during the exam.

Turning again to FIG. 2, the algorithm in block 210 reviews image data for cessation of transducer motion (as distinguished from cessation of motion in the body being examined, as discussed above with respect to the algorithms of block 212). For example, the algorithm of block 210 could be useful in conjunction with cardiology (echocardiography) exams. Specifically, it can be difficult to obtain a good view of a beating heart, particularly due to the motion of the heart. But a skilled sonographer can from time to time get a particular good view worth saving for later review. In such an event, it is likely that the sonographer will hold the transducer steady for a relatively longer period of time. By reviewing successive frames of image data for cessation in the very near field of view, e.g., in the first 1 to 2 centimeters from the face of the transducer, the image data can be compared for relative lack of motion of the transducer without the need to factor in the motion of the heart itself.

There are many algorithms that are known in the ultrasound art to compare the motion inherent in a series of ultrasound images (or portions of ultrasound images), any of which can be applied to the review called for by the algorithms in blocks 210 and 212 of the event recognition processor 120 in FIG. 2. By way of example and not limitation, motion estimation between successive image frames can be accomplished by cross-correlation of the images, summing the absolute differences between the images, or any other technique that is an approximation of these. Moreover, tracking only simple landmarks rather than all pixels, such as cysts, blood vessels, or highly reflective targets or other landmarks within the images, can save computational time.

Turning now to block 214 of FIG. 2, in a contrast-imaging exam, the event recognition processor 120 will apply an algorithm that targets increased rate of change of brightness in the image. When a contrast agent is injected into the patient, the brightness of the image quickly increases at the beginning of the exam, and then levels off. Images of the heart are particularly worth marking and/or storing during the period when the rate of change of brightness is greatest. Moreover, just as the sudden increase in change of brightness over time triggers a first distinguished event, the leveling off of the curve could trigger a second distinguished event of a pair of distinguished events. In other words, either the algorithm of block 214 in the event recognition processor in FIG. 2, or the algorithm in block 228 of the archival subsystem 118 in FIG. 3 could recognize the second distinguished event as a point at which to mark the end of the interesting part of the contrast examination, or at which to stop storing image data. In a different contrast agent protocol, known as destructive contrast imaging, ultrasound system 100 acts to destroy the contrast agent as quickly as possible. In this protocol, a graphical depiction of brightness over time would produce a different result from the classic contrast imaging protocol described above. But in either protocol, the "distinguished events" will be recognized by the rate of change of brightness (i.e., the slope of the brightness/time curve).

Finally, turning to the algorithm of block 216 of FIG. 2, in the case of a Color Doppler exam, the event recognition processor 120 will look for the presence of jets, or regions of high velocity, in the heart. The algorithm in this case would produce a histogram of velocities in the Color Doppler pan box. Unique events would be triggered by regions of high velocities, for example, significant velocities in the top 5% of the velocity scale around Nyquist. As before, the recognition of a distinguished event by block 218 of the event recognition processor 120 of FIG. 2 will trigger some or all of the post-processing steps of the archival subsystem 118 of FIG. 3. In this case, decimation by block 220 to reduce the number of frames stored is not likely to be desirable, because such jets are fast-moving and the maximum spatial and temporal resolution attainable is desired. On the other hand, the cropping of the image in block 224 could be advantageous, in that focusing on the relatively small portion of the image in the region of the high velocity jets could permit higher temporal resolution and/or lower image compression to be obtained. Block 226 might also be invoked, to retrospectively capture a first number of image frames before the jet, and a second number of image frames thereafter. Finally, in block 228, capture can be continued until a second distinguished event occurs, the second such event being the cessation of the jet. Accordingly, all the image frames that are bracketed by the jet and its cessation could be captured, as well as several frames before and after the pair of distinguished events. In a different embodiment, the duration of the captured image clip could be for a first fixed period of time before the first distinguished event, and a second fixed period of time thereafter.

Of course, many more examples are possible, and more than one set of event recognition algorithm blocks can be invoked for any one of the imaging modalities described here or used in any ultrasound system. For example, in a cardiology exam, it might be desirable to capture, as "distinguished events" instances where the probe is relatively still, on the assumption that the sonographer deemed the image to be one worthy of careful real-time study. In that case, not only would the event recognition processor screen to select regions of high velocity in the color pan box, but it would also look at the underlying B-mode image, for example in the first one to two centimeters in the near field, and select "distinguished events" based on when there is little or no motion in that region of the image. Moreover, contrast imaging could be performed as part of the same exam. Accordingly, in a comprehensive cardiology exam involving contrast imaging and an ECG, there might be occasion for the event recognition processor 120 to invoke algorithm blocks 208, 210, 214 and 216 at different stages of the process, or concurrently (in parallel). The output of the algorithm blocks 208, 210, 212, 214 and 216 can be passed, respectively, via paths 29, 30, 31, 32 and 33 to the distinguishing event decision block 218. If the distinguished event is detected, the event recognition processor sends a signal via path 20 to user interface 130 to alert the user, and also sends a signal via path 34 to the optional event and/or image characterization capability block 219 for further processing before proceeding via path 47 to the archival subsystem 118, described in further detail below in connection with FIG. 3.

As discussed with respect to the various examples of algorithm blocks in the event recognition processor 120, irrespective of how the distinguished events are identified, there are several ways in which the marking and/or storing of data can be effectuated. In one set of embodiments, the amount of material automatically marked or stored can be bounded temporally, such as in terms of a pre-selected number of image data sets before and after the occurrence of the distinguished event (where the numbers can be the same or different, and where they can be preset in the system, or optionally set by the sonographer). For example, in the case of an ECG trace, the event recognition processor might capture one or two heart cycles before and one or two heart cycles after a cycle of substantially shortened duration. The pre-selection can be pre-programmed into the system, e.g., as a pre-set on the basis of imaging modality, or could optionally be provided as a user-determined variable (which, ideally, the user would select before commencing the exam).

In an alternative set of embodiments, "pairs" of distinguished events can bound the marking and/or storing of data. In such case, the nature of each of the distinguished events in the pair may have opposite characteristics, and in some embodiments, a first one of the pair of distinguished events is marked with a start marker, and a second one of the pair of distinguished events is marked with an end marker. Thus, for example, the first distinguished event of the pair might be the cessation of movement of a fetus, while the second distinguished event of the pair might be the re-commencement of such motion. Similarly, in the case of a contrast imaging exam, the first distinguished event of the pair might be a sudden increase in brightness, while the second distinguished event of the pair might be a brightness level that is a predetermined fraction of the maximum brightness, or that is no more than a certain amount brighter than the image before introduction of the contrast agent.

In FIG. 2, once a distinguished event has been identified in block 218, the image data sets associated with the distinguished event are passed via path 34 to the event and/or image characterization capability 219. Here the image data are evaluated to determine characteristics about the nature of the distinguished event and/or the image itself, which characteristics could result in how the image data sets are processed, respectively, in blocks 220 and 224 of FIG. 3.

The event characterization capability 219 applies algorithms to determine the progress of the event being imaged, such as the rate of change in brightness in a contrast exam. Accordingly, at any given point during the contrast exam, the event characterization capability could determine what retention fraction is to be applied by decimation block 220 of the archival subsystem 118 of FIG. 3. For example, the decimation block 220 could apply relatively more decimation (a lower retention fraction) if successive images were relatively invariant, and relatively less decimation (a higher retention fraction) in the presence of a relatively high rate of change of any measured variable in the image. Thus, the event characterization capability 219 selects one or more retention states based upon characterization of a feature (such as motion, rate of brightness change, etc.), and causes fewer than all image data sets of the selected portion of the ultrasound examination to be stored, for some characterized features. Retention states can be implemented as a simple mapping of a retention fraction based on the feature characterization without regard to the imaging modality or application, or in other embodiments, retention states can be implemented as a function of the imaging modality or application as well as the characterization of the feature.

For the purposes of this description, the retention fraction is inverse to the level of decimation—i.e., a retention fraction of 1 means that 100% of the image data are stored, while a retention fraction of 0.5 means that only half of the image data sets are stored and a retention fraction of 0 means that none of the image data sets are stored. Of course, as will be appreciated by one of ordinary skill in the art, the decimation block will uniformly decimate an image clip or portion thereof for a given retention fraction, such that, for example, in the case of a retention fraction of 0.5, every other image data set would be retained, rather than retaining the first half of the image data sets and discarding the second half. On the other hand, the retention fraction could vary throughout the duration of an image clip, particularly, for example, in the case of contrast agent exams.

Accordingly, a distinguished event would be recognized by block 218 at the onset of the introduction of the contrast agent, triggering the passage of image data via path 34 to the event characterization block 219 and then the archival subsystem 118 as shown in FIG. 2. Event characterization block 219 reviews the image data associated with the distinguished event for the rate of change of brightness, and sends a signal to block 220 in FIG. 3 indicating the level of decimation to be applied. Relatively little or no decimation would be applied during an initial relatively steep part of a brightness vs. time curve, but as the rate of change of brightness slowed and the curve flattened, the image data could be decimated more aggressively.

The image characterization capability of block 219, on the other hand, applies algorithms to detect specific features in an image for the purpose of controlling block 224 in FIG. 3. It determines what portions of the field of view could be cropped in block 224 as being outside a portion of interest of the image. Conversely, the image characterization capability could determine the need to enlarge the user's selected pan box Region of Interest to include a relevant portion of the image that the user may have omitted. For example, algorithms designed to detect cardiac chamber boundaries can be used in connection with the functionality in cropping/enlarging block 224.

Returning to FIG. 3, in block 222, the archival subsystem 118 has the capability of marking image clips surrounding distinguished events for later review, meaning that a marker or flag is set where distinguished events occur in the series of images so that a sonographer or physician can "fast forward" to the sections of the exam that have been marked (much like book-marking a web page or a book). The advantage of marking each of a pair of distinguished events with different markers is that the post exam reviewer would likely want to skip through the exam based on the start markers, i.e., would want to start viewing from the first event of each pair and to fast forward to the next start marker at the last event of each pair. This forwarding and fast-forwarding functionality can be provided, for example, by the archival subsystem 118.

Alternatively or in addition, in block 228, the archival subsystem 118 has the capability of storing image data sets at and around such distinguished events. There are several options for storing such data sets shown in FIG. 3: archival internal hard disk 230 and capture memory 116 via paths 42 and 14 respectively; and external storage media 124, workstation 128 and network server 126, accessed via paths 44, 46 and 45 respectively (or paths 15, 19, and/or 18 respectively as illustrated in FIG. 1). When the images are stored in an external workstation 128, network server 126, or external storage media 124, it is preferable to include the DICOM headers. Accordingly, archival subsystem 118 includes block 250, accessed via pathway 41, for modifying multiframe images to be DICOM compliant.

Image data sets stored in external workstation 128, network server 126, or external storage media 124 can be passed via paths 49, 48 and 47 to the event recognition processor 120, processed there for event recognition, passed via path 13 to be further processed by archival subsystem 118, passed via path 14 to capture memory 116, and then via path 43 to be displayed on display 112 for further review after such processing. In such a manner, ultrasound examination data from external ultrasound systems can be sorted into concise files which are focused around distinguished events. Such files are more quickly and easily reviewed than files containing all of the ultrasound examination data.

It will be appreciated that while post-processing blocks 220, 222, 224 and 226 have been shown as running in series in FIG. 3, via respective paths 36, 37, 38 and 39, they could instead process the data in parallel.

Moreover, the interconnecting relationships between workstation 128, network server 126 and external storage media 124 differ between FIGS. 1 and 3, for the purpose of illustrating that a variety of image communication and storage configurations are possible and within the scope of this invention.

Simply for the purposes of illustration, the preferred embodiments described herein have included a substantial number of image storage blocks, such as the capture memory 116, the internal hard disk 230, the external storage media 124, the network server 126 and the workstation 128, but not all such blocks are necessary to carry out the invention, and in fact, the invention can be carried out with as few as one memory storage block. Similarly, while the preferred embodiments described herein have included a substantial number of algorithm blocks in the event recognition processor 120, as few as one of such blocks could be used in the intelligent ultrasound examination storage system, saving the sonographer the necessity of focusing simultaneously on the real-time ultrasound examination and the preservation of key data for later review.

Finally, this detailed description of preferred embodiments has allocated certain functional blocks to the event recognition processor 120, and others to the archival subsystem 118, but as a matter of design choice the features in the respective blocks can be merged, or partitioned differently. Thus, the event recognition processor 120 can itself perform the functions of automatically marking and or storing subsets of an ultrasound examination including one or more distinguished events, or it can send a signal to the archival subsystem 118—such as imaging data containing one or more distinguished events—which signal would cause the subsystem to automatically mark and/or store such subsets, and/or cull through pre-stored examinations and discard portions of such examinations not worthy of further review.

Accordingly, the invention is to be limited only by the appended claims and all equivalents thereto.

We claim:

1. In a diagnostic medical ultrasound system, the improvement comprising an event recognition processor, wherein said event recognition processor is configured:
   a. to recognize one or more non-cyclical distinguished events constituting a subset of an ultrasound examination, the ultrasound examination comprising a rolling stream of a series of ultrasound image data sets during a real-time examination, the recognition being based on analysis by the event recognition processor of the ultrasound image data sets of the ultrasound examination, wherein the one or more non-cyclical distinguished events are temporal events; and
   b. to select a portion being less than all of the ultrasound examination to be stored or marked based on the recognition of the one or more distinguished events, non-selected portions of the ultrasound examination including ultrasound image data sets after the one or more distinguished events, by performing at least one of the following:
      i. automatically marking the one or more events;
      ii. automatically causing the one or more events to be marked;
      iii. automatically storing the one or more events;
      iv. automatically causing the one or more distinguished events to be stored;
      v. automatically terminating storage of a portion of the ultrasound examination;
      vi. automatically causing termination of storage of a portion of the ultrasound examination; or
      vii. combinations thereof;
   further comprising an image characterization capability, wherein said image characterization capability is configured:
   a. to select a cropping factor based upon characterization of an image; and
   b. to cause less than an entire field of view of an image to be stored.

2. The invention of claim 1, wherein the event recognition processor recognizes a substantially stationary probe as the one or more distinguished events, the recognition being a function of motion represented by the ultrasound image data sets.

3. The invention of claim 1, wherein the event recognition processor recognizes a rate of change in brightness as the one or more distinguished events.

4. The invention of claim 1, wherein the event recognition processor recognizes a jet in Color Doppler as the one or more distinguished events.

5. The invention of claim 1, wherein the event recognition processor:
 a. recognizes a pair of distinguished events which brackets the portion of the ultrasound examination of interest; and
 b. selects the portion of the examination that occurs temporally in between the pair of distinguished events.

6. The invention of claim 5, wherein a first one of the pair of distinguished events is marked with a start marker, and a second one of the pair of distinguished events is marked with an end marker.

7. The invention of claim 6, wherein the event recognition processor also selects at least one of a first additional portion of the exam before the pair of distinguished events and a second additional portion of the exam after the pair of distinguished events.

8. The invention of claim 1, wherein the event recognition processor selects at least one of a first portion of the exam before each distinguished event and a second portion of the exam after each distinguished event.

9. The invention of claim 1, further comprising an event characterization capability, wherein said event characterization capability is configured:
 a. to select one or more retention states based upon event characterization of a feature in the selected portion of the ultrasound examination; and
 b. to cause fewer than all image data sets of the selected portion of the ultrasound examination to be stored for some characterized features.

10. The invention of claim 9, wherein the characterized feature is motion.

11. The invention of claim 9, wherein the characterized feature is a rate of change in brightness.

12. The invention of claim 1, wherein the event recognition processor provides feedback to a user interface to indicate that a distinguished event has been recognized.

13. The invention of claim 12, wherein the feedback is audible.

14. The invention of claim 13, wherein the feedback is a tone of a first pitch at the beginning of storage or marking of an image clip, and is a tone of a second pitch at the end of storage or marking of an image clip.

15. The invention of claim 12, wherein the feedback is visible.

16. The invention of claim 15, wherein the feedback is a recording icon.

17. The invention of claim 15, wherein the feedback is an incrementing displayed number.

18. The invention of claim 1, where the event recognition processor is configured to operate on either real time image data or stored image data.

19. The system of claim 1 wherein the event recognition processor is configured to recognize the one or more non-cyclical distinguished events automatically without user input of criteria for recognizing the one or more non-cyclical distinguished events.

20. In a diagnostic medical ultrasound system, the improvement comprising an intelligent examination storage system, said intelligent examination storage system comprising an event recognition processor with an event characterization capability configured to automatically recognize from image analysis and to mark or store one or more non-repeating subsets of an ultrasound examination, the ultrasound examination comprising a rolling stream of a series of ultrasound image data sets of a feature during a real-time examination, said event characterization capability selecting, based on event characterization of the feature, said one or more non-repeating subsets to be bracketed by one or more pairs of distinguished events determined as a function of the image analysis of the feature comprising motion in the ultrasound examination, portions of the ultrasound examination after at least one pair of the one or more pairs of distinguished events not being marked or stored.

21. The improvement of claim 20, wherein the event recognition processor automatically marks a first event of each pair with a start marker and a second event of each pair with an end marker.

22. The improvement of claim 21, wherein the intelligent examination storage system marks or stores, or causes to be marked or stored, image data sets between the start and end markers, as well as a preview subset of the ultrasound examination occurring before the start marker and a post-view subset of the ultrasound examination occurring after the end marker.

23. The improvement of claim 22, wherein the intelligent examination storage system marks or stores, or causes to be marked or stored, image data before and after the non-repeating subset of the ultrasound examination.

24. The improvement of claim 20, wherein said intelligent examination storage system comprises an image characterization capability.

25. A method for storing data by a diagnostic medical ultrasound system, the method comprising:
 a. inputting ultrasound examination data event recognition processor comprising a sequence of image data sets to an event recognition processor;
 b. processing the examination data with the event recognition processor by:
  i. reviewing the sequence of image data sets;
  ii. determining, as a result of the reviewing, whether a non-cyclical distinguished event has occurred;
  iii. if a distinguished event has occurred, selecting a subset of the image data sets for marking and storage, or for cessation of marking and storage;
 c. marking or storing the selected subset of the image data sets, or stopping the marking and/or storage of the selected subset of the image data sets, without the need for user intervention;
 wherein motion between sequential image data sets is reviewed, and the determination of whether a distinguished event has occurred is based upon the absence of substantial motion above a pre-determined motion threshold.

26. The method of claim 25, further comprising as part of step biii, selecting for the subset of the image data sets, at least one of a first additional portion of the exam before the distinguished event and a second additional portion of the exam after the distinguished event.

27. The method of claim 26, further comprising in step biii, decimating between image data sets as part of the selecting step.

28. The method of claim 25, wherein the motion that is reviewed is motion of the probe.

29. The method of claim 25, wherein the motion that is reviewed is motion within the image.

30. The method of claim 25, further comprising in step b, processing the examination data based on an application-specific pre-set or an imaging modality.

31. The method of claim 30, wherein brightness between sequential image data sets in a cardiology examination is reviewed, and the determination of whether another distinguished event has occurred is based upon a rate of change of brightness exceeding a pre-determined threshold.

32. The method of claim 30, wherein velocity information in a Color Doppler image is compared, and the determination of whether another distinguished event has occurred is based upon a rate of change of high velocities.

33. The method of claim 25, further comprising in step b, determining whether a pair of distinguished events has occurred.

34. The method of claim 33, further comprising marking or storing at least some of the image data sets between one or more pairs of distinguished events.

35. The method of claim 34, further comprising marking or storing at least some of the image data sets before the one or more pairs of distinguished events.

36. The method of claim 35, further comprising marking or storing at least some of the image data sets after the one or more pairs of distinguished events.

37. The method of claim 25, wherein in the inputting step, the sequence of image data sets is input from a stored ultrasound exam.

38. The method of claim 25, wherein step b further comprises an event characterization capability, wherein said event characterization capability is configured:
   a. to select one or more retention states based upon characterization of a feature in the selected portion of the ultrasound examination; and
   b. to cause fewer than all image data sets of the selected portion of the ultrasound examination to be stored for some characterized features.

39. The method of claim 25 wherein (b)(ii) comprises determining whether the event occurs within the sequence where the sequence is acquired in an on-going manner during a real-time ultrasound examination.

40. The method of claim 25 wherein (b)(ii) comprises determining whether a transition event occurs.

41. A method for storing data by a diagnostic medical ultrasound system, the method comprising:
   a. inputting ultrasound examination data comprising a sequence of image data sets to an event recognition processor;
   b. processing the examination data with the event recognition processor by:
      i. reviewing the sequence of image data sets;
      ii. determining, as a result of the reviewing, whether a non-cyclical distinguished event has occurred;
      iii. if a distinguished event has occurred, selecting a subset of the image data sets for marking and storage, or for cessation of marking and storage;
   c. marking or storing the selected subset of the image data sets, or stopping the marking and storage of the selected subset of the image data sets, without the need for user intervention;
   further comprising in step b, applying a cropping factor before storing, and storing frames cropped by said cropping factor.

* * * * *